US005798332A

United States Patent [19]

Sinha et al.

[11] Patent Number: 5,798,332

[45] Date of Patent: Aug. 25, 1998

[54] GLYCOSYLATION-MEDIATED INHIBITION OF FACTOR X

[75] Inventors: Uma Sinha, San Francisco; David L. Wolf, Palo Alto, both of Calif.

[73] Assignee: COR Therapeutics, Inc., South San Francisco, Calif.

[21] Appl. No.: 302,226

[22] Filed: Sep. 6, 1994

Related U.S. Application Data

[63] Continuation of Ser. No. 854,109, Mar. 20, 1992, abandoned.

[51] Int. Cl.$^6$ .......................... A61K 38/16; A61K 38/36; A61K 38/43

[52] U.S. Cl. .............................. 514/8; 514/2; 424/94.1; 424/94.5; 530/380; 530/381; 530/384

[58] Field of Search ............................ 424/94.1, 94.5; 530/380, 381, 384; 514/8, 2

[56] References Cited

U.S. PATENT DOCUMENTS

| | | | |
|---|---|---|---|
| 4,668,621 | 5/1987 | Doellgast et al. | 435/13 |
| 4,742,046 | 5/1988 | Bliah | 514/8 |
| 5,059,654 | 10/1991 | Hou et al. | 525/54.1 |
| 5,190,919 | 3/1993 | Fair et al. | 514/15 |
| 5,453,272 | 9/1995 | Heerze et al. | 424/190.1 |

OTHER PUBLICATIONS

Sata, T.; et al., American Journal of Pathology, vol. 139(6), Dec. 1991, pp. 1435–1448.

Chattopadhay, A; et al., The Journal of Biological Chemistry, vol. 264(19), Jul. 5, 1989, pp. 11035–11043.

Jesty, J; et al., The Journal of Biological Chemistry, vol. 250(12), Jun. 25 1975, pp. 4497–4504.

Freussinet, J., FEBS Letters, vol. 124(1), Feb. 1981, pp. 48–52.

Yin, E.T. et al., J. of Biological Chemistry, vol. 246(11), pp. 3694–3702, Jun. 1971.

Hortin, G.L. et al., Analytical Biochemistry, vol. 188(2), pp. 271–277, 1990.

Engel, A.M. Thromb. Haemostasis, vol. 46(1), p. 297, abstract #0934, 1981.

Seegers, W.H. et al., Thrombosis Research, vol. 1(5), pp. 443–460, 1972.

Louis D. Herze et al.; "Comparison of the Lectin-Like Activity of Pertussis Toxin with Two Plant Lectins That Have Differential Specificities for α(2–6) and α(2–3)-Linked Sialic Acid" Biochemical and Biophysical Research Communication; vol. 172, No. 3; Nov. 15, 1990; pp. 1224–1229.

Duffy et al., *J. Biol. Chem.*, vol. 267, pp. 7821–7827 (1992) Apr. (issue #11).

Inoue et al., *Eur. J. Biochem.*, vol. 218, pp. 153–163 (1993).

Nakagawa et al., *Glycoconjugate Journal*, vol. 12, pp. 173–181 (1995).

Okamoto et al., *J. Inher. Metab. Dis.*, vol. 16, pp. 435–440 (1993).

Hoover et al., *Cell* (1978) 14:423–428.

Etingin et al., *Cell* (1990) 61:657–662.

Davie, E.W., *Haemostasis and Thrombosis*, Second Edition, R.W. Coleman et al., eds., (1987) J.B. Lippencott, Philadelphia, PA, Chapter 6, pp. 242–267.

Furie et al., *Cell* (1988) 53:505–518.

Steinberg et al., *Haemostasis and Trombosis*, Second Edition, R.W. Colman et al., eds., (1987) J.B. Lippencott, Philadelphia, PA, Chapter 7 pp. 112–119.

Di Scipio et al., *Biochemistry* (1977) 16:5253–5260.

Watzke et al., *J. Biol. Chem.* (1990) 285:11982–11989.

Nesheim et al., *J. Biol. Chem.* (1979) 254:10952:10962.

Nesheim et al., *J. Biol. Chem* (1981) 256(13):6537–6540.

Skogen et al., *J. Biol. Chem.* (1984) 259(4):2306–2310.

Krishnaswamy et al., *J. Biol. Chem.* (1988) 263(8):3823–3824.

Husten et al., *J. Biol. Chem.* (1987) 262(27):12953–12961.

Girard et al., *Nature* (1989) 338:518–520.

Girard et al., *Science* (1990) 248:1421–1424.

Dunwiddie et al., *J. Biol. Chem.* (1989) 264:16694–16699.

Waxman et al., *Science* (1990) 248:593–596.

Titani, *Proc. Natl. Acad. Sci.* (1975) 72:3082–3086.

Fair et al., *J. Clin. Invest.* (1979) 648:884–894.

Mizouchi et al., *J. Biol. Chem.* (1980) 255:3526–3531.

Hase et al., *J. Biol. Chem.* (1990) 265:1858–1861.

*Primary Examiner*—Leon B. Lankford, Jr.
*Assistant Examiner*—Francisco C. Prats
*Attorney, Agent, or Firm*—Morgan, Lewis & Bockius LLP

[57] ABSTRACT

Reagents that specifically bind a carbohydrate target wherein sialic acid is linked at the nonreducing terminus of a glycoside to a galactose or galactosamine residue through an α2-6 linkage are able to inhibit the conversion of human Factor X to human Factor Xa. These reagents (SA/Gal/GalNAc binding reagents) as well as other strategies for inhibiting the conversion of Factor X to Factor Xa are useful in treating thrombosis, inflammation and other conditions associated with excess thrombin activity.

18 Claims, 2 Drawing Sheets

GLYCOSYLATION-MEDIATED INHIBITION OF FACTOR X

This application is a continuation of application Ser. No. 07/854,109, filed 20 Mar. 1992 now abandoned.

TECHNICAL FIELD

The invention relates to agents that inhibit the activation of Factor X, and thus are candidates for treatment or prevention of thrombosis. More specifically, the invention concerns agents that affect the normal glycosylation pattern of Factor X and thus diminish its conversion to its activated form. The activated form of Factor X, Factor Xa, is essential for the formation of thrombin, which is, in turn, essential for the formation of blood clots, as well as an inducer of smooth muscle cell proliferation.

BACKGROUND ART

Thrombin is a multifunctional protease that regulates several key biological processes. For example, thrombin is among the most potent of the known platelet activators. In addition, thrombin is essential for the cleavage of fibrinogen to fibrin to initiate clot formation. These two elements are involved in normal hemostasis but in atherosclerotic arteries can initiate the formation of a thrombus, a major factor in pathogenesis of vasoocclusive conditions such as myocardial infarction, unstable angina, nonhemorrhagic stroke and reocclusion of coronary arteries after angioplasty or thrombolytic therapy. Thrombin is also a potent inducer of smooth cell proliferation and may therefore be involved in a variety of proliferative responses such as restenosis after angioplasty and graft-induced atherosclerosis. In addition, thrombin is chemotactic for leukocytes and may therefore play a role in inflammation. (Hoover, R. J., et al. *Cell* (1978) 14:423; Etingin, O. R., et al., *Cell* (1990) 61:657.) These observations indicate that inhibition of thrombin formation or inhibition of thrombin itself may be effective in preventing or treating thrombosis, limiting restenosis and controlling inflammation.

The formation of thrombin is the result of the proteolytic cleavage of its precursor prothrombin at the Arg-Thr linkage at positions 271–272 and the Arg-Ile linkage at positions 320–321. This activation is catalyzed by the prothrombinase complex, which is assembled on the membrane surfaces of platelets, monocytes, and endothelial cells. The complex consists of Factor Xa (a serine protease), Factor Va (a cofactor), calcium ions and the acidic phospholipid surface. Factor Xa is the activated form of its precursor, Factor X, which is secreted by the liver as a 58 kd precursor and is converted to the active form, Factor Xa, in both the extrinsic and intrinsic blood coagulation pathways. It is known that the circulating levels of Factor X, and of the precursor of Factor Va, Factor V, are on the order of $10^{-7}$M. There has been no determination of the levels of the corresponding active Factors Va and Xa.

The complete amino acid sequences of human Factor X and Factor Xa are known, and are as described by Davie, E. W., in *Hemostasis and Thrombosis,* Second Edition, R. W. Coleman et al., eds. (1987) p. 250. Factor X is a member of the calcium ion binding, gamma carboxyglutamyl (Gla)-containing, vitamin K dependent, blood coagulation glycoprotein family, which also includes Factors VII and IX, prothrombin, protein C and protein S (Furie, B., et al., *Cell* (1988) 53:505).

The mature Factor X protein is preceded by a 40-residue pre-pro leader sequence which is removed during intracellular processing and secretion. The mature Factor X precursor of Factor Xa is then cleaved to the two-chain form by deletion of the three amino acids RKR between the light chain C-terminus and activation peptide/heavy chain N-terminus. Finally, the two chain Factor X is converted to Factor Xa by deletion of the 52 amino acid "activation peptide" sequence generating a light chain of 139 residues and a heavy chain of 254 residues. These are linked through a single disulfide bond between position 128 of the light chain and position 108 of the heavy chain. The light chain contains the Gla domain and an epidermal growth factor-like domain; the protease activity resides in the heavy chain and involves the histidine at position 42, the aspartic at position 88, and a serine at position 185.

Bovine Factor X has also been studied, and the amino acid sequence of bovine Factor X has been reported by Titani, K., *Proc Natl Acad Sci USA* (1975) 72:3082–3086. The activation peptide of bovine Factor X is 51 amino acids long and contains almost equal masses of polypeptide and carbohydrate (Discipio, R. G. et al., *Biochemistry* (1977) 16:5253).

There are two known pathways for the activation of the two-chain Factor X in vivo. Activation must occur before the protease is incorporated into the prothrombinase complex (Steinberg, M., et al., in *Hemostasis and Thrombosis,* Coleman, R. W., et al. eds. (1987) J.B. Lippencott, Philadelphia, Pa., p. 112). In the intrinsic pathway, Factor X is cleaved to release the 52-amino acid activation peptide by the "tenase" complex which consists of Factor IXa, Factor VIIIa and calcium ions assembled on cell surfaces. In the extrinsic pathway, the cleavage is catalyzed by Factor VIIa which is bound to a tissue Factor on membranes. Factor X may also be converted to Factor Xa by in vitro cleavage using a protease such as that contained in Russel's viper venom. This protease is described by DiScipio, R. G., et al., *Biochemistry* (1977) 6:5253.

Factor X variants exist that are differentially activated in the extrinsic versus intrinsic pathway (Fair, D. S. et al., *J Clin Invest* (1979) 648:884–894). For example, Factor X "Vorarlberg" has 15% of the activity of normal Factor X with respect to the extrinsic pathway but 75% of normal Factor X with respect to the intrinsic pathway (Watzke, H. H. et al., *J Biol Chem* (1990) 265:11982–11989).

Clearly, the action of thrombin in platelet aggregation and clot formation could be prevented by suitable manipulation of factor X/Xa, in view of the essential role of factor Xa in the formation of thrombin from its precursor.

The activity of Factor Xa in effecting the conversion of prothrombin to thrombin is dependent on its inclusion in the prothrombinase complex. Therefore, one approach to this manipulation has been directed to preventing the participation of factor Xa in the thrombinase complex. The formation of the prothrombinase complex (which is 278,000 fold faster in effecting the conversion of prothrombin to thrombin than Factor Xa in soluble form) has been studied (Nesheim, H. E., et al., *J Biol Chem* (1979) 254:10952). These studies have utilized the active site-specific inhibitor, dansyl glutamyl glycyl arginyl (DEGR) chloromethyl ketone, which covalently attaches a fluorescent reporter group into Factor Xa. Factor Xa treated with this inhibitor lacks protease activity, but is incorporated into the prothrombinase complex with an identical stoichiometry to that of Factor Xa and has a dissociation constant of $2.7\times10^{-6}$M (Nesheim, M. E., *J Biol Chem* (1981) 256:6537–6540; Skogen, W. F., et al., *J Biol Chem* (1984) 256:2306–2310; Krishnaswamy, S., et al., *J Biol Chem* (1988) 263:3823–3824; Husten, E. J., et al., *J Biol Chem* (1987) 262:12953–12961).

Other approaches to inhibition of Factor Xa include the use of lipoprotein-associated coagulation inhibitor (LACI), now called tissue factor pathway inhibitor (TFPI) (Girard, T. J., et al., *Nature* (1989) 338:518; Girard, T. J., et al., *Science* (1990) 248:1421), leech-derived antistatin (Dunwiddie, C. T., et al., *J Biol Chem* (1989) 264:16694), and tick-derived TAP (Waxman, L., et al., *Science* (1990) 248:593). Alternatively, agents which inhibit the vitamin K-dependent Gla conversion enzyme, such as coumarin, have been used. None of these approaches have proved satisfactory due to lack of specificity, the large dosage required, toxic side effects, and the long delay in effectiveness.

PCT publication US 91/06337 discloses an additional approach wherein the active site of Factor Xa is modified to prevent its enzymic activity while retaining the ability to form the prothrombinase complex.

The invention's approach is directed to the inhibition of the conversion of Factor X to its active form, Factor Xa. Specifically, this mode of inhibition is directed to manipulation of the glycosylation residues associated with Factor X.

Bovine, but not human, Factor X has been subjected to detailed studies with respect to its glycosylation patterns. The heavy chain of bovine Factor X contains N-linked glycosylation at residue 36 and O-linked glycosylation at residue 300 (Mizuochi, T. et al., *J Biol Chem* (1980) 255:3526–3531). While the glycosylation pattern of human Factor X is not known, it has been noted that the activation peptide contains two potential N-linked glycosylation sites at positions 39 and 49 (Davie, E. W., in "Hemeostasis and Thrombosis", Second Edition, R. W. Coleman eds. (1987) p. 250). In addition, serine-linked sugar residues have been reported on the first epidermal growth factor-like domain of the related bovine factor IX (Hase, S. et al., *J Biol Chem* (1990) 265:1858–1861); analogously, the EGF-like domains on human Factor X light chain may contain O-linked sugars.

Accordingly, the invention offers an alternative approach to inhibit the conversion of Factor X to Factor Xa, thus preventing formation of an active prothrombinase complex.

DISCLOSURE OF THE INVENTION

The invention provides effective therapeutic agents for the prevention and treatment of thrombus formation and other pathological processes in the vasculature induced by thrombin such as restenosis and inflammation. This is highly significant as thrombus formation is the leading cause of death in Western societies, and restenosis is an expanding problem with increased use of angioplasty and other invasive procedures. The therapeutic materials of the invention are capable of preventing or of diminishing the generation of human Factor Xa.

These pharmaceuticals are especially useful in acute settings to prevent thrombosis. This includes preventing thrombus formation in the coronary arteries of patients with rest angina, preventing rethrombosis after thrombolysis, and prevention of thrombosis during complicated angioplasties. These pharmaceuticals will also be useful in preventing smooth muscle cell proliferation following angioplasty or other vascular invasive procedures. The invention therapeutics offer considerable advantage over the now standard treatment which involves heparin (Hanson, R. S., et al., *Proc Natl Acad Sci* (1988) 85:3184). In one embodiment, the compounds of the invention are lectins that specifically bind the carbohydrate moieties associated with human Factor X, thus preventing its conversion to Factor Xa. In another embodiment, the compounds of the invention are themselves capable of altering the glycosylation structure.

In one aspect, the invention is directed to a method to inhibit human Factor X activation, which method comprises contacting human Factor X with a specific carbohydrate-binding reagent capable of binding the terminal sialic acid-linked (α2-6) to a galactose or N-acetyl galactosamine residue. These target glycosyl residues are abbreviated herein SA(α2-6)Gal and SA(α2-6)GalNAc, respectively. The reagents are "SA/Gal/GalNAc" binding reagents. The carbohydrate-binding reagent, when contacted with Factor X under suitable conditions of time, temperature and pH, is effective to prevent the conversion of human Factor X to human Factor Xa by either the extrinsic or intrinsic pathway. Thus, in another aspect, the invention is directed to a complex comprising said carbohydrate binding reagent and Factor X.

In another aspect, the invention is directed to factors which render Factor X unsusceptible to activation by cleavage of the carbohydrate moieties to which it is derivatized, or by inhibiting the sialylation of this Factor.

Other aspects of the invention include pharmaceutical compositions of the therapeutically useful carbohydrate-binding or carbohydrate cleavage reagents and to methods to prevent or treat thrombosis or other pathological events initiated by thrombin using these compositions.

MODES OF CARRYING OUT THE INVENTION

Figure 1A:
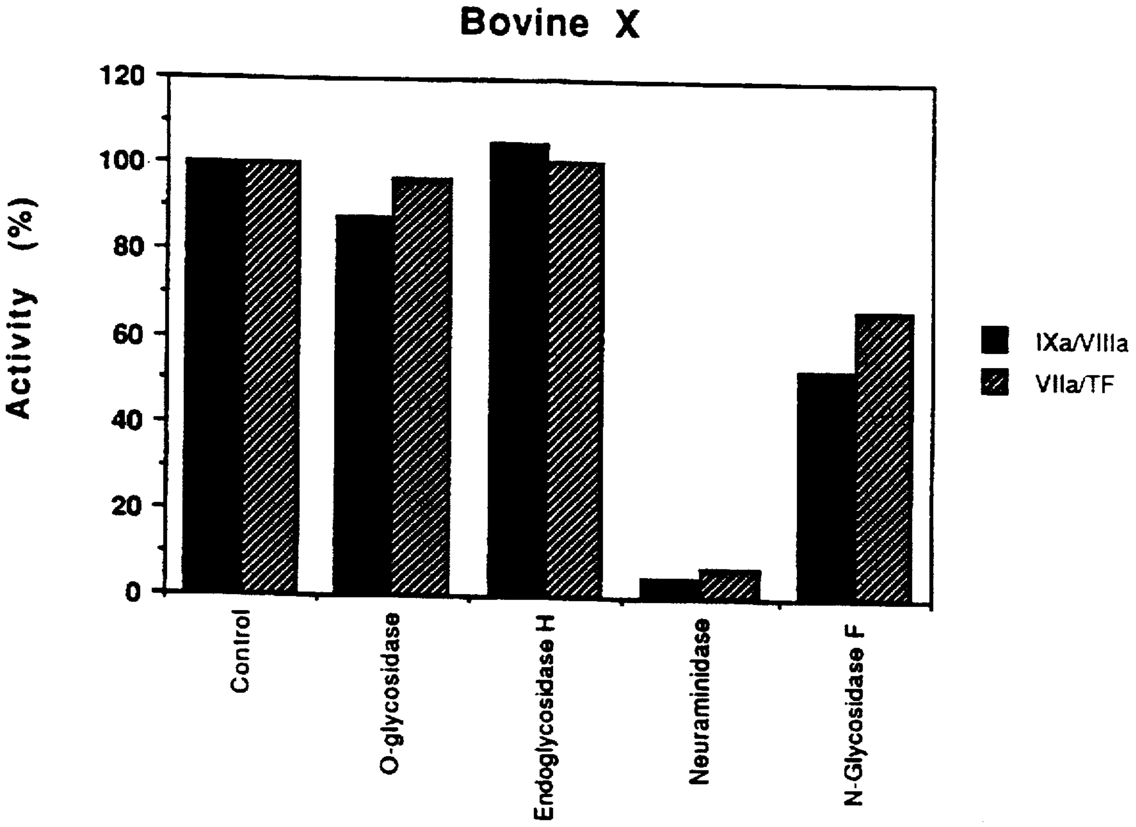
FIGS. 1A and 1B show the results of glycosidase treatment of bovine Factor X and human Factor X, respectively, with respect to the coagulation activation of these factors.

The invention is based on the discovery that blockage of specific carbohydrate residues or cleavage of the carbohydrate moieties in human Factor X effectively inhibit its conversion to its activated form which is essential for the formation of the prothrombinase complex. Specifically, those reagents which are capable of binding to sialic acid residues at the non-reducing terminus of the glycosylation moieties, wherein the sialic acid residues linked (α2-6) to galactose or N-acetyl galactosamine residues (SA/Gal/GalNAc binding reagents) are capable of this inhibition. These reagents include various lectins, such as *Sambucus nigra* agglutinin (SNA) (elderberry bark lectin), and certain mammalian lectins, as well as other small molecules, such as peptides which are known, or can be shown, to bind this target. In particular, peptides derived from Factor IXa/VIIIa or from tissue factor/VIIa are useful in this respect.

An additional important class of SA/Gal/GalNAc binding reagents are antibodies specifically immunoreactive with this target. Such antibodies can conveniently be produced by rendering either of these disaccharide moieties immunogenic through coupling to immunogenicity-conferring carriers such as keyhole limpet hemocyanin, human serum albumin, bovine serum albumin, diphtheria toxoid, rotavirus VP6 carrier protein, and the like. Suitable techniques for coupling carbohydrates to immunogenic carriers of this type, for example coupling the carbonyl moiety of the carbohydrate to an available amino group on the carrier followed by reduction, are well known in the art.

The disaccharide moiety, coupled itself or in the context of a larger carbohydrate to an immunogenicity-conferring carrier, is then administered in standard immunization protocols to suitable subjects to induce the production of antibodies. The effectiveness of the protocols can be monitored by standard immunoassays on the sera of the injected animals using the immunogen, or preferably the relevant disaccharide portion thereof, as antigen, i.e., specific binding partner. Such immunoassays, such as radioimmunoassay, enzyme-linked immunoassays, fluorescence-type immunoassays, and the like are well known in the art. When sufficient titers are obtained, the antisera may be used directly after purification of the immunoglobulins, or the antibody-producing cells such as the spleen cells or as peripheral blood lymphocytes of the immunized animals can be used for the production of monoclonal forms of these antibodies immunospecific for the disaccharide moiety. In general, techniques for immortalization of the antibody-producing cells in the form of, for example, hybridomas for the production of such antibodies, are also now standard procedure.

In addition to these SA/Gal/GalNAc binding reagents, antibodies, including monoclonal antibodies, that bind generally to the carbohydrate moieties of the activation peptide of Factor X may inhibit Factor Xa formation.

In an alternative approach, prevention of the formation of the sialyl termination residues of the glycosylated Factor X may be an effective way of providing a Factor X that resists activation. In one approach, administration of inhibitors of (α2-6)sialyl transferase to the organism can achieve this end. Thus, the organism will produce Factor X which is devoid of the essential substitutent needed for its activation. In a variation of this approach, inhibitors of the transferases which catalyze the glycosylation of Factor X in general are also effective, since the internal saccharide chains must be provided as acceptors for the sialyl residue. The inhibitors are supplied to the organism in a manner effective to alter its repertoire of glycosylated Factor X. These inhibitors thus behave as preventive as well as prophylactic agents with regard to conditions characterized by an excess of Factor Xa or which are benefited by a diminution in the levels of Factor Xa. Examples of such inhibitors include Amphomycin, Castanospermine, 2,3-Dehydro-2-deoxy-N-acetyl-neuraminic acid, 1-Deoxymannojirimycin hydrochloride, 1-Deoxynojirlmycin, N-Methyl-1-deoxynojirlmycin, Swainsonine and Ttunicamycin.

In still another approach, a soluble analog of the SA/Gal/GalNAc sequence that is evidently required for Factor X-to-Factor Xa conversion may be used as a competitor for the essential disaccharide residue. Such competitors are introduced so as to be present under those conditions wherein Factor X-to-Factor Xa conversion would otherwise be achieved. Thus, in vitro, the soluble analog is introduced along with the components of the intrinsic or extrinsic pathway for conversion. In the context of a whole living organism, the soluble analog is administered to prevent this conversion in situ. The soluble analogs are low molecular weight molecules which have space and charge contours similar to those of the SA(α2-6)Gal or SA(α2-6)GalNAc residues as they occur on the glycosylation side chains of Factor X. Among such soluble analogs are SA(α2-6)Gal and SA(α2-6)GalNAc per se, as well as analogous di- and trisaccharides or alternative complex structures which exhibit these characteristics.

In still another alternative, Factor X-to-Factor Xa conversion can be inhibited by reagents that remove the glycosylation moieties from Factor X, thus rendering it unsusceptible to activation. Suitable such agents include neuraminidases and certain specific glycosidases that remove sialyl residues.

The preferred method for inhibiting Factor X-to-Factor Xa conversion untilizes binding reagents that are capable of forming complexes with the SA(α2-6)Gal and SA(α2-6)GalNAc residues on the glycosylation side chains of Factor X. In general, reagents that are useful SA/Gal/GalNAc binding reagents for use in the method of the invention can be identified using simple specific binding assays with the disaccharide moiety, or a molecule containing same, as the specific binding partner for the candidate compound to be tested. Such assays are conducted in a manner analogous to immunoassays wherein, for example, in a typical protocol, the disaccharide moiety to be targeted is coupled to a solid support and the coupled support treated with the candidate reagent. The treated support is then washed to remove any unbound candidate. Candidate remaining bound to the support is detected by any suitable means such as by an additional moiety which specifically binds the candidate which is itself labeled using a detectable label, for example a radiolabel or enzyme label. Thus, candidate SA/Gal/GalNAc binding reagents can be quickly screened for efficacy in such simple and straightforward protocols.

In the invention method, the SA(α2-6)Gal and/or SA(α2-6)GalNAc binding agent, as identified by the above method, is contacted with the Factor X whose conversion is to be inhibited. The resultant of such contact is a complex which is resistant to conversion to the active form by either the extrinsic or intrinsic pathway. Said contacting is with an excess of said reagent, preferably a 2- to 10-fold molar excess and at temperature, pH, and salt conditions appropriate for the formation of the complex. Generally such contacting is at 4° C. to room temperature for 4 hours to overnight and in the presence of physiological saline and pH.

The SA/Gal/GalNAc binding compounds of the invention that are lectins may be prepared by isolation of native sources or, under some circumstances, may be prepared recombinantly. Alternatively, synthetic peptides containing the SA/Gal/GalNAc binding domain may be substituted for the full-length lectins. These peptides may be synthesized using standard solid-phase or solution-phase peptide synthesis techniques as are known and indeed commercially available in the art.

The SA/Gal/GalNAc binding reagents of the invention and alternative methods set forth above that are capable of inhibiting the activation of Factor X are useful in procedures complicated by thrombosis and in conditions whose pathogenesis involves thrombin generation. These conditions include those involving arterial thrombosis, such as unstable (i.e., rest) angina and abrupt vessel closure during vascular interventions including coronary and peripheral angioplasty and atherectomy, and during and after vascular bypass procedures (peripheral and coronary), reocclusion after thrombolytic therapy for myocardial infarction, thrombotic stroke (stroke in evolution), and thrombosis due to vasculitis (Kawasaki's disease). Also included are conditions involving venous thrombosis, such as deep venous thrombosis of the lower extremities, pulmonary embolism, renal vein, hepatic vein, inferior vena cava thrombosis, and cavernous sinus thrombosis. Other target conditions are those involving diffuse activation of the coagulation system, such as sepsis with disseminated intravascular coagulation, disseminated intravascular coagulation in other settings, thrombotic thrombocytopenic purpura, and rare conditions of unknown etiology (Lupus anticoagulant).

The SA/Gal/GalNAc binding agents of the invention and alternative methods for inhibition of Factor X activation are also useful as an anticoagulant and anti-inflammatory for cardiopulmonary bypass, in harvesting organs, in preparation of blood products or samples and in transport and implantation of organs and associated treatment of the recipient. These reagents and methods are especially useful in a slow release form in indwelling intravascular devices (i.v.s, catheters, grafts, patches).

Thrombosis also plays a role in restenosis following vascular interventions such as angioplasty, atherectomy, or endarterectomy by directly or indirectly causing smooth muscle cell proliferation, and the reagents of the invention are also useful in treating this condition.

Adult respiratory distress syndrome (ARDS) is thought to be an "endotoxin" disease in which a prothrombotic endothelium is likely to exist, with inflammatory and proliferative components; the invention reagents and methods are also useful in treatment of ARDS.

The therapeutic reagents of the invention which are lectins or their peptide-binding domains or which are antibodies or fragments thereof, or other peptide-based substances are formulated for administration using excipients conventional for administration of proteins or peptides, typically by injection, as set forth, for example, in *Remington's Pharmaceutical Sciences,* Mack Publishing Company, latest edition, Easton, Pa. For the antithrombosis effect, the lectins or other peptides or proteins are administered systemically, preferably by injection, and preferably by intravenous injection. Dosage levels depend on a number of factors, including the condition of the subject and the specific embodiment chosen. However, suitable dosage ranges are on the order of 1–50 mg per patient per continuous injected dose. For injection, the protein is dissolved or suspended in liquid medium, for example, Hank's solution, Ringer's solution, dextrose solution, and various buffers. Additional excipients such as stabilizers can also be employed.

Besides injection, the lectins or other therapeutic agents of the invention can be administered systemically, via suppository, oral administration, transmucosal administration, including intranasal sprays, and by slow release formulations. Additional formulation techniques include encapsulation formulations, such as liposomes.

In addition to utility as a therapeutic, the invention reagents can be used to raise polyclonal antisera or to produce cells which can be fused to immortalizing partners to obtain sources of monoclonal antibodies specific for these reagents. These antibodies are useful as diagnostic tools to monitor therapy with the invention reagents.

The ability of the SA/Gal/GalNAc binding reagents of the invention or other candidate substances to inhibit the conversion of Factor X to Factor Xa can be studied by determining the effect of the candidate inhibitor on the ability of Factor X subjected to putative activation conditions characteristic of the extrinsic or intrinsic pathway to generate an enzymic activity characteristic of Factor Xa. Thus, the presence of generated Factor Xa can be measured by kinetics of hydrolysis of chromozym X (N-methoxycarbonyl-D-norleucyl-glycyl-arginine-4-nitranilide acetate, Boehringer Mannheim) hydrolysis. (Wolf, D. L., et al., *J Biol Chem* (1991) 266:13726–13730.)

To generate the putative Factor Xa enzymes by the intrinsic pathway, Factor X is activated with 0.2 nM Factor IXa, 6.8 nM Factor VIIIa (from Cutter hemophilia concentrate), excess phospholipids in the mM range, and 5–10 mM calcium ions. The activation is conducted by incubating Factor X in physiological saline for about 10 min at 37° C. and detecting the Factor Xa formed by the chromozym X hydrolysis described above. Activation of Factor VIII to VIIIa is conducted as described by Hill-Eubanks, D. C., *J Biol Chem* (1990) 17854–17858.

To determine the effect of the SA/Gal/GalNAc binding reagent, the Factor X and the candidate binding reagent are first preincubated at low temperature for 4–24 hours in buffered saline containing approximately 1 mM each of calcium, magnesium and manganese ions. Similarly, candidate inhibiting enzymes which remove the glycosylation of Factor X are preincubated with this factor prior to addition of the components of the intrinsic pathway. To test the inhibitory ability of the competitive soluble analogs of the SA/Gal/GalNAc residues, the soluble analog is added along with the components of the pathway. This assay method is, however, not appropriate for those agents that are inhibitors of glycosylation, as the effect of these inhibitors is dependent on Factor X formation in the living organism.

For effect on the extrinsic pathway, the Factor X to Factor Xa conversion is conducted (as described for the intrinsic pathway activation) using 0.5–1 nM Factor VII, tissue factor (thromboplastin C), excess phospholipids and 5–10 mM calcium ions.

The foregoing procedures are illustrative of the manner in which candidate compounds which are SA/Gal/GalNAc binding reagents or which otherwise inhibit Factor Xa formation may be confirmed to show inhibition of Factor X activation. These assay procedures are used to determine the effectiveness of a glycosidase or other reagent capable of removing glycosylation units as well as the SA/Gal/GalNAc binding agents in the inhibition of the activation of Factor X. The assays set forth above are used as described, including pre-incubation with the candidate glycosidase or other glycosylation-removing enzymes or with the SA/Gal/GalNAc binding agent, and concomitant with soluble analogs of the SA/Gal/GalNAc sequence.

The following examples are intended to illustrate, but not limit the invention.

EXAMPLE 1

Ability of Lectins of Various Binding Specificities to Complex with Human and Bovine Factor X In a preliminary experiment, the ability of lectins with various binding specificities to complex with human and bovine Factor X and Xa was tested using the glycan differentiation kit (First Choice, Boehringer-Mannheim). In the procedure, conducted according to the manufacturer's instructions, the Factor X or Factor Xa was first immobilized on nitrocellulose or nylon membrane, and the specific binding of digoxygenin-labeled lectins from the kit was detected using antidigoxygenin antibody coupled to alkaline phosphatase. Table 1 summarizes the results obtained using the various lectins of the kit.

TABLE 1

| | | Bovine | | Human | |
|---|---|---|---|---|---|
| Lectin | Specificity | X | Xa | X | Xa |
| Galanthus nivalis agglutinin (GNA) | High mannose chains | – | – | – | – |
| Peanut agglutinin (PNA) | Gal(β1–3)GalNAc, (w/o SA) | – | – | – | – |
| Datura stramionium agglutinin (DSA) | Gal(β1–4)GalNAc; GlcNAc | – | – | + | – |

TABLE 1-continued

| | | Bovine | | Human | |
|---|---|---|---|---|---|
| Lectin | Specificity | X | Xa | X | Xa |
| Sambucus nigra agglutinin (SNA) | SA(α2-6)Gal SA(α2-6)GalNAc | − | − | + | − |
| Maackia amurensis agglutinin (MAA) | SA(α2-3)Gal | + | − | + | − |

Thus, DSA, SNA and MAA bind to human Factor X, and bovine Factor X is bound only by MAA. None of the activated forms bind to these lectins.

EXAMPLE 2

Inhibition of Factor X Activation in the Intrinsic Pathway

Human or bovine Factor X (1 μM) and the candidate lectin (5 μM) were incubated overnight at 4° C. in buffered saline containing 1 mM each of $Ca^{+2}$, $Mg^{+2}$ and $Mn^{+2}$ ions. The incubation mixtures were activated with Factor IXa, VIIIa, phospholipids and calcium ions as described hereinabove. The Factor Xa liberated was assayed using the chromozym X substrate described above. None of the lectins inhibited the activation of bovine Factor X; only SNA inhibited the activation of human Factor X. The extent of inhibition was 41%.

EXAMPLE 3

Inhibition of Factor X Activation by the Extrinsic Pathway

Bovine or human Factor X was incubated with the 5 lectins of Example 1 in the same manner as set forth in Example 2 and then activated with Factor VIIa, tissue factor, phospholipids and calcium ions as described hereinabove. Generation of Factor Xa was determined as above. None of the lectins inhibited activation of bovine Factor X; again only SNA inhibited the activation of human Factor X (67% inhibition).

EXAMPLE 4

Dose Dependence of Human Factor X Activation by SNA

Human Factor X (1 μM) was incubated with concentrations of SNA ranging from 0–20 μM overnight at 4° C. Aliquots were assayed using intrinsic and extrinsic pathway activators as described in Examples 2 and 3 above. Bovine Factor X was used as a control, and showed only slight inhibition at the highest concentration of SNA.

In the intrinsic pathway activation using IXa/VIIIa, virtually no inhibition was observed up to 1 μM SNA; at a concentration of 1.5 μM, inhibition was 40%, increasing to about 47% at 20 μM.

In the extrinsic activation pathway, virtually no inhibition was obtained at 0.5 μM SNA; however, 1 μM SNA showed an inhibition of about 27%, which increased to an inhibition of 80% at 20 μM SNA.

EXAMPLE 5

Effect of Various Glycosidases

Glycosidases of various specificities were used to treat human and bovine Factor X by treating Factor X with the glycosidase according to the manufacturer's instructions. In general, digestion is conducted at 37° C. overnight, although neuraminidase gave complete digestion after shorter time periods. The reaction mixtures were subjected to SDS/PAGE, followed by staining with Coomassie blue, and the shift in mobility of the treated Factor X proteins, as compared to untreated Factor X, was determined. Neither bovine nor human Factor X showed a shift in mobility for the light chain for any of the glycosidases. Certain of the glycosidases tested, however, did result in alteration of mobility of the heavy chain as set forth in Table 2 below.

The effects of deglycosylation on activity was tested in several ways. First, the deglycosylated material was tested in standard coagulation assays—the activated partial thromboplastin time assay (APTT) and the prothrombin time assay (PT). The assays were conducted using standard procedures but with Factor X-deficient human plasma and using an automatic coagulometer. The results of these assays are also shown in Table 2.

Figure 1B:
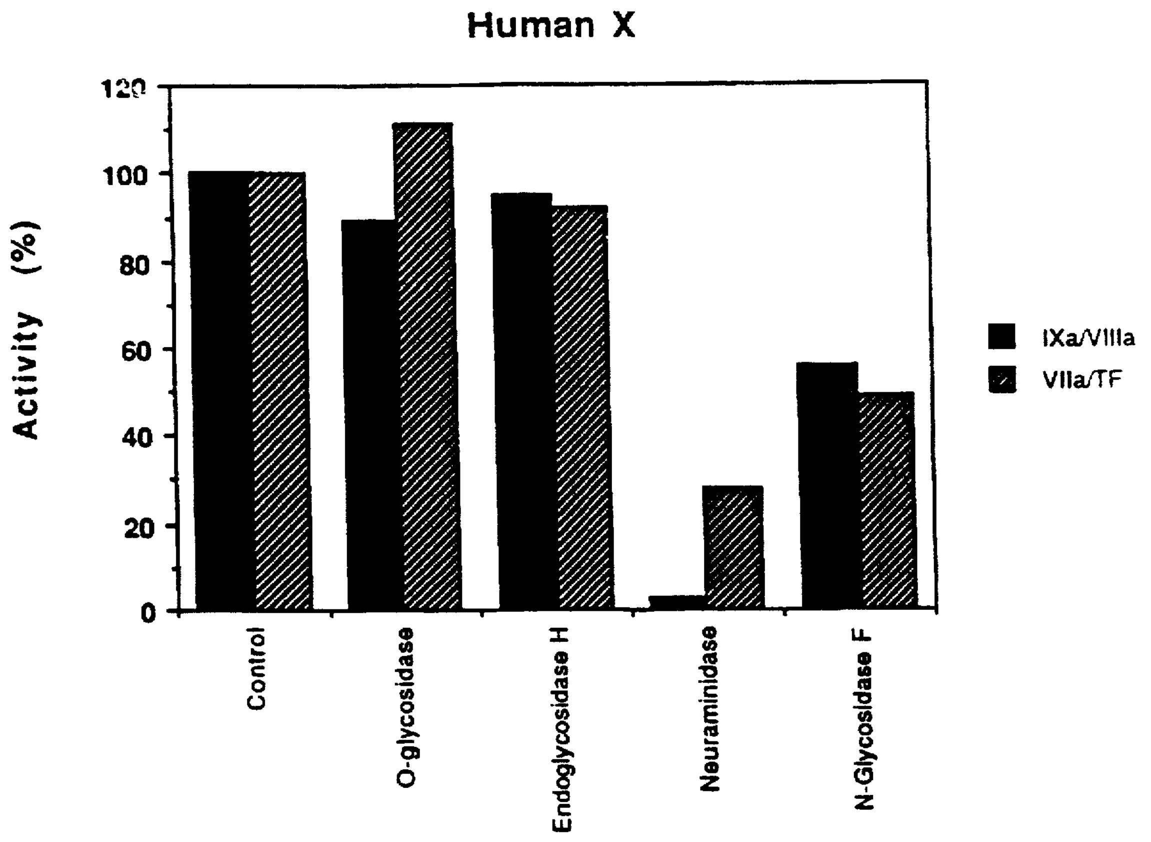

In addition, the glycosidase-treated proteins were activated using the Factor IXa/VIIIa complex or the Factor VIIa/tissue factor complex and the activated Factor Xa detected using chromozym X. These results are shown in FIGS. 1A and 1B for bovine Factor X and human Factor X, respectively.

TABLE 2

| | Human X | | | Bovine X | | |
|---|---|---|---|---|---|---|
| | ΔH.C. (kd) | APTT | PT | ΔH.C. (kd) | APTT | PT |
| Control | — | 100 | 100 | — | 100 | 100 |
| O-glycosidase | 6.2 | 61 | 108 | 3.3 | 116 | 106 |
| Endoglycosidase H | 0 | 49 | 60 | 0 | 88 | 106 |
| Neuraminidase | 4.5 | 12 | 8 | 4.5 | 4 | 2 |
| N-glucosidase F | 7 | 148 | 37 | 7 | 97 | 102 |

Table 2 shows, in addition to the shifts in heavy chain mobility, the results of the APTT and PT coagulation tests as a percentage of the activity of the control. Only neuraminidase was dramatically effective in reducing coagulation activity; however, endoglycosidase H was partially effective with respect to human Factor X.

FIGS. 1A and 1B show the results for bovine Factor X and human Factor X, respectively, in activation by the extrinsic or intrinsic pathways and assayed by chromozym X. Consistent with the results in the coagulation activities in Table 2, only neuraminidase is effective in substantially reducing the activation by either pathway.

We claim:

1. A method to treat thrombosis and conditions whose pathogenesis involves thrombin generation in a human subject, which method comprises administering to a subject in need of such treatment an amount of a reagent that binds to SA(α2-6)Gal or SA(α2-6)GalNAc or a pharmaceutical composition thereof effective to inhibit thrombosis.

2. A method to treat inflammation resulting from thrombosis or conditions whose pathogenesis involves thrombin generation in a human subject, which method comprises administering to a subject in need of such treatment an amount of a reagent that binds to SA(α2-6)Gal or SA(α2-6)GalNAc or pharmaceutical composition thereof effective to inhibit said inflammation.

3. A method to treat restenosis resulting from thrombosis and conditions whose pathogenesis involves thrombin generation in a human subject, which method comprises administering to a subject in need of such treatment an amount of a reagent that binds to SA(α2-6)Gal or SA(α2-6)GalNAc or pharmaceutical composition thereof effective to inhibit said restenosis.

4. A method to treat inflammation as a complication of transplantation, said inflammation resulting from thrombosis and conditions whose pathogenesis involves thrombin generation in a human subject, which method comprises administering to a subject in need of such treatment an amount of a reagent that binds to SA(α2-6)Gal or SA(α2-6)GalNAc or pharmaceutical composition thereof effective to inhibit thrombotic complications of transplantation.

5. The method according to any one of claims 1–4 wherein said reagent is selected from the group consisting of lectins, antibodies specifically immunoreactive to SA(α2-6) Gal or SA(α2-6)GalNAc, and peptides derived from Factors IXa/VIIIa or from tissue factor/Factor VIIa that specifically bind with SA(α2-6)Gal or SA(α2-6)GalNAc.

6. A method to inhibit the conversion of human Factor X to human Factor Xa which method comprises treating human Factor X with a reagent that binds to SA(α2-6)Gal or SA(α2-6)GalNAc in an amount and for a time sufficient to inhibit said conversion.

7. A method to identify a reagent that inhibits the conversion of human Factor X to human Factor Xa, which method comprises;

treating a disaccharide moiety which is SA(α2-6)Gal or SA(α2-6)GalNAc with a reagent;

assessing whether said reagent binds or does not bind to said disaccharide; and determining whether any reagent that binds to said disaccharide inhibits the conversion of human Factor X to human Factor Xa.

8. The method of claim 7 wherein said reagent is a lectin.

9. The method of claim 8 wherein the lectin is a mammalian lectin.

10. A complex comprising human Factor X and a reagent identified by the method of claim 7 that binds to a disaccharide moiety which is SA(α2-6)Gal or SA(α2-6)GalNAc and that inhibits conversion of human Factor X to human Factor Xa.

11. A complex comprising human Factor X and a reagent that binds to SA(α2-6)Gal or SA(α2-6)GalNAc.

12. A complex comprising human Factor X and *Sambucus nigra* agglutinin (SNA).

13. A method of identifying a reagent that inhibits the conversion of human factor X to human factor Xa, which method comprises:

(a) coupling a disaccharide moiety to a solid support, wherein the disaccharide moiety is SA(α2-6)Gal or SA(α2-6)GalNAc present on the glycosylation side chains of human Factor X;

(b) treating the solid support with a candidate reagent which may bind to the disaccharide moiety SA(α2-6) Gal or SA(α2-6)GalNAc;

(c) washing the treated support to remove any unbound reagent;

(d) detecting any reagent that remains bound to the support; and (e) further assessing whether the reagent that binds to SA(α2-6)Gal or SA(α2-6)GalNAc inhibits conversion of human Factor X to human Factor Xa.

14. A method to prevent thrombosis in a human subject, which method comprises administering to a subject in need of such treatment an amount of a reagent that binds to SA(α2-6)Gal or SA(α2-6)GalNAc or a pharmaceutical composition thereof effective to inhibit thrombosis.

15. A method to prevent inflammation resulting from thrombosis in a human subject, which method comprises administering to a subject in need of such treatment an amount of a reagent that binds to SA(α2-6)Gal or SA(α2-6)GalNAc or pharmaceutical composition thereof effective to inhibit said inflammation.

16. A method to prevent restenosis resulting from thrombosis in a human subject, which method comprises administering to a subject in need of such treatment an amount of a reagent that binds to SA(α2-6)Gal or SA(α2-6)GalNAc or pharmaceutical composition thereof effective to inhibit said restenosis.

17. A method to prevent inflammation as a complication of transplantation, said inflammation resulting from thrombosis in a human subject, which method comprises administering to a subject in need of such treatment an amount of a reagent that binds to SA(α2-6)Gal or SA(α2-6)GalNAc or pharmaceutical composition thereof effective to inhibit thrombotic complications of transplantation.

18. The method according to any one of claims 14–17, wherein said reagent is selected from the group consisting of lectins, antibodies specifically immunoreactive to SA(α2-6) Gal or SA(α2-6)GalNAc, and peptides derived from Factors IXa/VIIIa or from tissue factor/Factor VIIa that specifically bind with SA(α2-6)Gal or SA(α2-6)GalNAc.

* * * * *